March 4, 1941. J. D. BROWNELL Plant Pat. 458
ROSE
Filed July 18, 1940
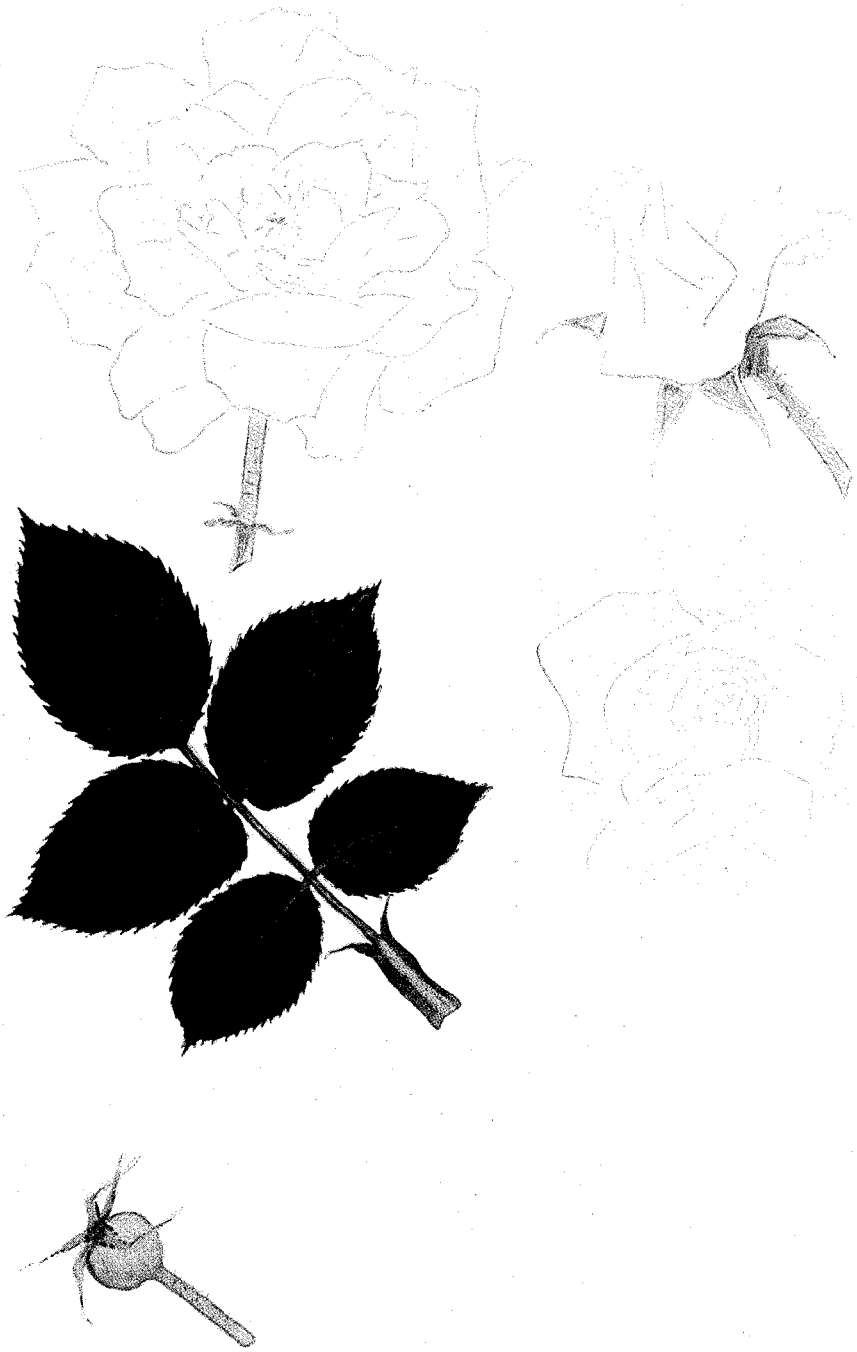
Josephine D. Brownell
INVENTOR.

Patented Mar. 4, 1941

Plant Pat. 458

UNITED STATES PATENT OFFICE

458

ROSE

Josephine D. Brownell, Little Compton, R. I.

Application July 18, 1940, Serial No. 346,162

1 Claim. (Cl. 47—61)

My invention relates to roses and especially to a new, original and distinct variety of the class known commercially as hardy climbing roses and to a subdivision thereof known as large flowering *Rosa wichuraiana* hybrid; produced by me and under my direction in the breeding grounds of gardens in Little Compton, Rhode Island, by cross pollinating, which can be and has been asexually reproduced.

My new rose is new as to the following characteristics and especially as to their joint association in connection with the characteristics of hardiness and immunity from serious injury on account of cold temperatures prevailing in certain parts of the northern portion of the United States;

The unique orange toned color of the petals, being approximately spectrum orange (ordinary dictionary definition) in total effect of both sides of the petals;

The multiple petals and variation within certain definite limits of the form of the bloom;

Its character of fragrance;

Its climbing and branching habit;

In the accompanying drawing forming a part of this specification I have shown my new rose in its natural colors, that is as near as is possible to do so artificially.

I otherwise describe my new rose as follows;

It is a large flowered hardy climbing hybrid *Rosa wichuraiana*, crossed in its ancestral generations with, in addition to *Rosa wichuraiana* several hybrid tea and species roses.

It is otherwise described as follows

*Essential information*

Type: Hardy climbing; outdoor; seedling; for cut flowers, garden display and for pot forcing.

Class: Hybrid climbing *wichuraiana*; subdivision, large flowered climber.

Breeding: The pollination that produced this new rose was planned and directed by me and was made July 3, 1935* in my garden; the seed therefrom was planted in December 1935 and germinated at the Brightridge Greenhouses at East Providence, Rhode Island, in March 1936, for me and at my request. The plant therefrom was planted in my breeding grounds in Little Compton, Rhode Island, in May 1936. This plant can be and has been by me asexually reproduced by budding in my gardens in the months of July and August 1936–7–8–9 inclusive; these propagations reproduced the characters of the original seedling.

The genealogy of this new rose variety is to the best of my knowledge and belief as follows, the seed parent is the climbing rose commercially known as "Golden Glow" and the pollen parent is the rose commercially known as the sub-zero hybrid tea variety "Break O'Day," both of which were produced by me and under my direction, by cross breeding.

The cross which produced this new rose variety was planned by me and made by me and under my directions in the following manner: the seed parent was first emasculated and covered with a bag for protection against self and foreign pollen; this was removed and pollen applied with a brush and the bag was replaced. In the previous generation the crosses which produced both of the parents were made in the same manner.

Propagation: It has held its distinguishing characteristics through succeeding propagation by budding.

*Flower*

Habit: It blooms out of doors in Little Compton, Rhode Island, in late June and July and begins to bloom about five days before the variety Mary Wallace begins to bloom.

Flowers borne: Singly to eight, occasionally more; in regular hybrid tea type of clusters, which usually develop consecutively a few days' maturity apart, on strong stiff woody stems, varying in length up to 15 and 20 or more inches in length.

Quantity of bloom: Abundant out of doors in full sunshine, not materially reduced by covering established plants with clean earth for winter protection. Under favorable conditions it blooms the year after budding, from wood grown the year of budding and can be grown to bloom as two year old plants, even when promptly transplanted.

Continuity: One season of three to five weeks according to age and size of plant.

Fragrance: Strong and pleasing under favorable environment; sweet, slightly pungent and aromatic, being China tea in combination with *Rosa wichuraiana* and musk.

Bud: Size, medium long pointed, open well, being not at all affected by wet or hot weather at Little Compton.

*This and other dates herein are approximate.

Peduncle, medium in length and size, erect, stiff, color nearly Bice Green (color references unless otherwise noted are to Ridgway) edged slightly darker, somewhat overlaid with Dahlia Carmine, nearly smooth with a few short reddish hairs. Foliaceous appendages occasionally extending about one-quarter inch beyond the tips of the bud.

Color: as calyx breaks and bud begins to open and until fully open, outer petals both sides are nearly Orange at (1) (reference to Plate I Yellow Range opposite page 256 of The Rose Manual by J. H. Nicolas 1930) outside slightly more reddish. Inside fades to Nasturtium at (2) Plate II Salmon Range, (same reference), changing later to Nankin at (3) to Aurora at (3) to flesh at (3). Outside fades slowly to Coral at (2) to Salmon at (3) to Aurora at (3), (all same reference).

Bloom: Is usually four to five inches in diameter when fully open; of hybrid tea form and type, double having petals variable in number usually averaging around twenty seven, frequently with a small number of central narrow petals or petaloids in addition. The flower opens high centered and in moderate temperatures with recurled petals. The pistils and stamens are concealed until flower is nearly completely open.

The petals are in form somewhat variable from obovate, frequently notched at apex, innermost petals frequently irregular in form. Texture substantial and leathery, both sides slightly satiny to shiny and notably brilliant.

Color of opening flower same as described for opening bud.

The colors of the flower are resistant to fading and hold notably long, yet they do fade before the petals fall, to a lighter color.

The petals usually drop off cleanly.

Reproductive organs: The stamens are slightly variable and moderate in number, color Apricot at (20) (Nicolas), edges of anthers are Deep Chrome (Ridgway) as they open to release pollen.

Stigmas are same color as stamens to slightly lighter, lower portion of styles overlaid with Spectrum Red (Ridgway).

Filaments are medium in length.

Pistils are few to medium in number, of slightly uneven length. One ovary infrequently protrudes from the calyx lobe.

*Plant*

Foliage: Abundant, of compound leaflets, frequently three in number near the flower and five lower on the stems and seven occasionally on lower end of flower stems and usually seven on canes and branches.

The leaflets are ovate to somewhat narrower with moderately acute apexes and bases rounded to slightly acute. Edges moderately serrate. The leaflets are thick and glossy and medium leathery.

The color of the leaflets is upper side Medium Dark Green to Forest Green, under side Bice Green with a slight overlay of a composite of the petal colors (these and the following color references except where noted are to Ridgway).

The petioles are medium with miniature hairs on upper sides or edges and small prickles on the under sides, all substantially the same color as the under sides of the leaves except variously tinged with Dahlia Carmine; the prickles turn lighter at maturity.

The stipules are medium in length and width, with normal points that spread in relation to each other about 90 degrees. The edges have minute hairs.

Canes are medium large and branching, color of the bark is nearly Bice Green shading to Dahlia Carmine. The prickles are Dahlia Carmine to slightly variable turning to lighter and more colorless.

Growth: Medium vigorous, comparable in vigor with Mary Wallace. Habit is nearly erect to about 75 degrees from the horizontal, except angle of flower stem is somewhat more erect. Prickles medium, usually straight to slightly bent downward at tips, size medium to small, small hairs on peduncle and pedicel.

Winter resistance: From tests already made it seems to be resistant fully exposed to temperatures of about ten degrees below zero Fahrenheit, or slightly more resistant than Mary Wallace and Dr. W. van Fleet.

Comparisons: The hardy climbing rose varieties in commerce most closely resembling this new rose variety are Albertine, Jacotte, Coralie, Apricot Glow and Coral Creeper. This new rose is distinctly different from all of these in that its color is of a greater intensity of the orange tones and the form of the flower is different and the petals are more recurled.

I claim:

The hardy hybrid *Rosa wichuraiana* climbing rose variety, characterized by its vigorous branching growth, its glossy green foliage, its hybrid tea type of flower and cluster, the pleasing fragrance and double petalage of its flowers, with color and form substantially as described and shown, the color shades combining into a self color of nearly spectrum orange.

JOSEPHINE D. BROWNELL.